United States Patent [19]

Naeder

[11] Patent Number: 5,064,438

[45] Date of Patent: Nov. 12, 1991

[54] ARTIFICIAL JOINTLESS FOOT

[75] Inventor: Max Naeder, Duderstadt, Fed. Rep. of Germany

[73] Assignee: Otto Bock Orthopaedische Industrie Besitz- und Verwaltungs-Kommanditgesellschaft, Duderstadt, Fed. Rep. of Germany

[21] Appl. No.: 268,620

[22] Filed: Nov. 7, 1988

Related U.S. Application Data

[63] Continuation of Ser. No. 54,447, May 27, 1987, abandoned.

[30] Foreign Application Priority Data

Dec. 29, 1986 [DE] Fed. Rep. of Germany ....... 3644613

[51] Int. Cl.$^5$ .............................................. A61F 2/66
[52] U.S. Cl. ......................................... 623/55; 623/53
[58] Field of Search .................................. 623/53-55, 623/56

[56] References Cited

U.S. PATENT DOCUMENTS

| | | | |
|---|---|---|---|
| 3,940,804 | 3/1976 | Benton | 623/55 |
| 4,007,497 | 2/1977 | Haupt | 623/55 |
| 4,089,072 | 5/1978 | Glabiszewshi | 623/53 |
| 4,360,931 | 11/1982 | Hampton | 623/55 X |
| 4,506,395 | 3/1985 | Haupt | 623/53 |
| 4,555,817 | 12/1985 | McKenrick | 623/40 |
| 4,652,266 | 3/1987 | Truesdell | 623/55 |

FOREIGN PATENT DOCUMENTS

| | | | |
|---|---|---|---|
| 0390864 | 3/1924 | Fed. Rep. of Germany | 623/55 |
| 0806983 | 6/1951 | Fed. Rep. of Germany | 623/53 |
| 3309777 | 9/1984 | Fed. Rep. of Germany | . |
| 0479033 | 2/1916 | France | 623/53 |
| 0661071 | 7/1929 | France | 623/53 |
| 0377350 | 4/1940 | Italy | 623/53 |
| 0101054 | 3/1941 | Sweden | 623/53 |
| 0638675 | 10/1983 | Switzerland | 623/53 |
| 0105293 | of 1917 | United Kingdom | 623/53 |
| 1434413 | 5/1976 | United Kingdom | 623/55 |

OTHER PUBLICATIONS

Campbell Childs, Inc., Phoenix, Oreg., U.S.A.; p. 1-9.
The Seattle Foot; Alignment and Installation Manual; Mrs. M+Ind., Seattle, Wash., pp. 1-8.
Van Nostrand's Scientific Encyclopedia, 1983, p. 1692.
Stedman's Medical Dictionary, 1966.
Herkimer, Herbert, "Engineers' Illustrated Thesaurus", 1952.

Primary Examiner—David J. Isabella
Assistant Examiner—David H. Willse
Attorney, Agent, or Firm—Foley & Lardner

[57] ABSTRACT

An artificial jointless foot comprises an incompressible core, preferably made of wood, the underside of which slopes upwards from the front to the rear and forms an upper connecting surface in the ankle region and which extends into the instep region of the foot with an extension decreasing in height towards the front, a heel wedge connected to the underside of the core and made of a soft plastic foam, with a skin-forming layer composed of a plastic foam and completely surrounding the arrangement comprising the core and heel wedge, with the exception of an upper connecting surface. The foot has good movement properties, while at the same time being of simple design and having desirable flexibility in the instep region. The core, beginning from its front edge on the connecting surface, extending into the instep region by an amount corresponding to less than half its length on the connecting surface. A flexible inner foot made of plastic foam extends into the toe region and is likewise enclosed by the skin-forming layer. The inner foot adjoins the front surface of the core and the front side of the heel wedge. The skin-forming layer is a soft, easily deformable plastic foam layer, the restoring forces of which are less than the restoring forces of the inner foot.

20 Claims, 1 Drawing Sheet

ARTIFICIAL JOINTLESS FOOT

This application is a continuation of application Ser. No. 054,447, filed May 27, 1987, now abandoned.

BACKGROUND OF THE INVENTION

The present invention relates to an artificial jointless foot having an incompressible core, preferably made of wood, the underside of which slopes upwards from the front to the rear and forms an upper connecting surface in the ankle region and extends into the instep region of the foot with a portion decreasing in height towards the front, a heel wedge connected to the underside of the core and made of soft plastic foam, and a skin-forming layer made of plastic foam and completely surrounding the arrangement comprising the core and plastic foam heel wedge, with the exception of the upper connecting surface.

An artificial jointless foot is disclosed in German Patent Specification 3,309,777. The essential advantage of this foot is that the skin-forming layer protects the inner structure against the penetration of moisture and aggressive materials. The incompressible core extends very far into the instep region and ends approximately in the ankle region of the artificial foot. Adjacent to the front side of the core there is only the skin-forming layer which determines the flexibility of the foot in the toe and ankle region, together with a sheet-like fabric insert fastened to the underside of the front edge of the core and extending to the toes. The fabric insert stabilizes the foot against twisting in the ankle region. The soft heel wedge attached under the core in the heel region is likewise enclosed by the skin-forming layer. The skin forming layer, because it is relatively hard and having a weight per unit volume of the plastic foam of approximately 6 g/cm$^3$, should have only a small wall thickness of approximately 2 mm in the region of the heel wedge so as not to excessively impair the elastic properties of the very soft heel wedge. With this foot, the rolling action is determined first by the soft heel wedge surrounded by a relatively hard wall and then by the bending of the skin-forming layer in the ankle and toe region of the foot. The foot acquires relative rigidity because of the incompressible core extending into the ankle region.

A product catalog of Campbell Childs Inc., Phoenix, Oreg., USA, discloses a foot structure which is called the S.A.F.E. Foot and in which an incompressible core is provided in the ankle region only. An elongate inner foot extending into the toe region adjoins the front side of this core. Approximately in the region of the center of the foot, the inner foot is hollowed out on its underside, so that at this location there is an appreciable thinning of material which defines a bending region for the inner foot. The inner foot and the core, with the exception of the upper connecting surface, are surrounded by a relatively rigid foam which at the same time forms the heel wedge. Strips of elastic band extend from the core underneath the inner foot and are anchored to the inner foot at the tip thereof. A further strip of elastic band extends from the front side of the core directly into the material of the inner foot. In comparison with the foot mentioned in the introduction, this foot offers the advantage of flexibility, even in the instep region. This foot is extremely expensive due to the measures needed to stabilize the foot by means of the strips of elastic band. Furthermore, the inner structure of the foot is not protected against the penetration of water or aggressive agents.

SUMMARY OF THE INVENTION

It is therefore an object of the present invention to provide an artificial jointless foot having resilience over a very wide range of the rolling action.

It is also an object of the present invention to provide an artificial jointless foot having an incompressible core that extends into the instep region.

It is a further object of the present invention to provide an artificial jointless foot having a skin-forming layer which primarily serves the function of protecting the inner structure of the foot against penetration of water and aggressive agents.

Another object of the present invention is to provide an artificial jointless foot of a simple design, without reinforcing bands or the like, which guarantees a perfect rolling action and, at the same time, has flexibility even in the instep region.

In accordance with one aspect of the present invention, these objects are achieved by an artificial jointless foot comprising:

a) an incompressible core which comprises an underside which slopes upwards from the front to the rear;
   an upper connecting surface disposed in an ankle region of the foot, and
   an extension forwardly extending into an instep region of the foot, the extension decreasing in height towards the front, wherein the core extends horizontally from a front edge on the upper connecting surface into the instep region by an amount corresponding to less than about half of the length on the connecting surface;
b) a heel wedge connected to the underside of the core;
c) a flexible inner foot member adjoining both a front surface of the core and a front side of the heel wedge, the inner foot member extending into a toe region of the foot;
d) a soft, easily deformable skin-forming layer completely surrounding the core, the inner foot member and the heel wedge, with the exception of the upper connecting surface of the core, such that the restoring force of the skin-forming layer is less than the restoring force of the inner foot.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

An illustrative embodiment of the invention is described in further detail below and is represented schematically in the drawing, in which.

DETAILED DESCRIPTION OF THE PREFERRED EMBODIMENTS

Figure 3:
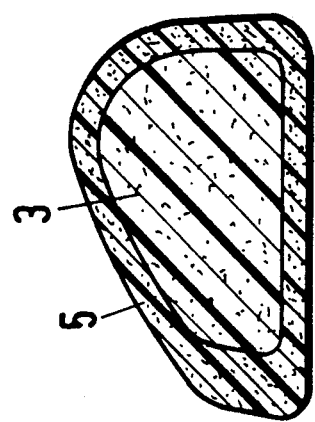
FIG. 3 shows a front view of a cross-section of the foot taken along the line III in FIG. 1.
Figure 1:
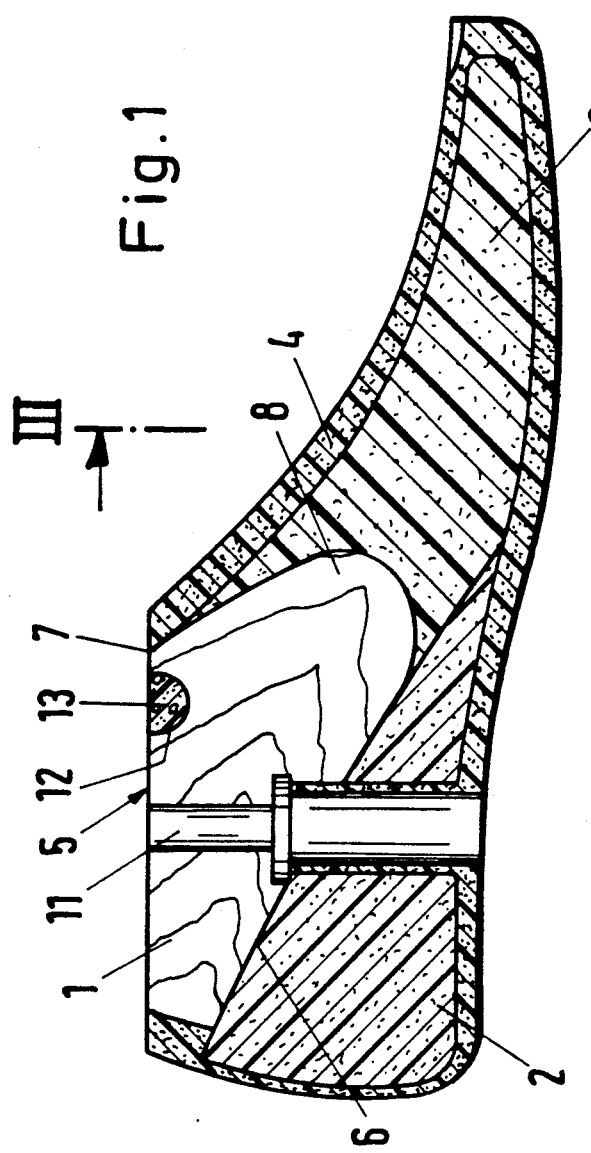
FIG. 1 shows a front view of a longitudinal section through an artificial foot taken along the line I—I in FIG. 2.
Figure 2:
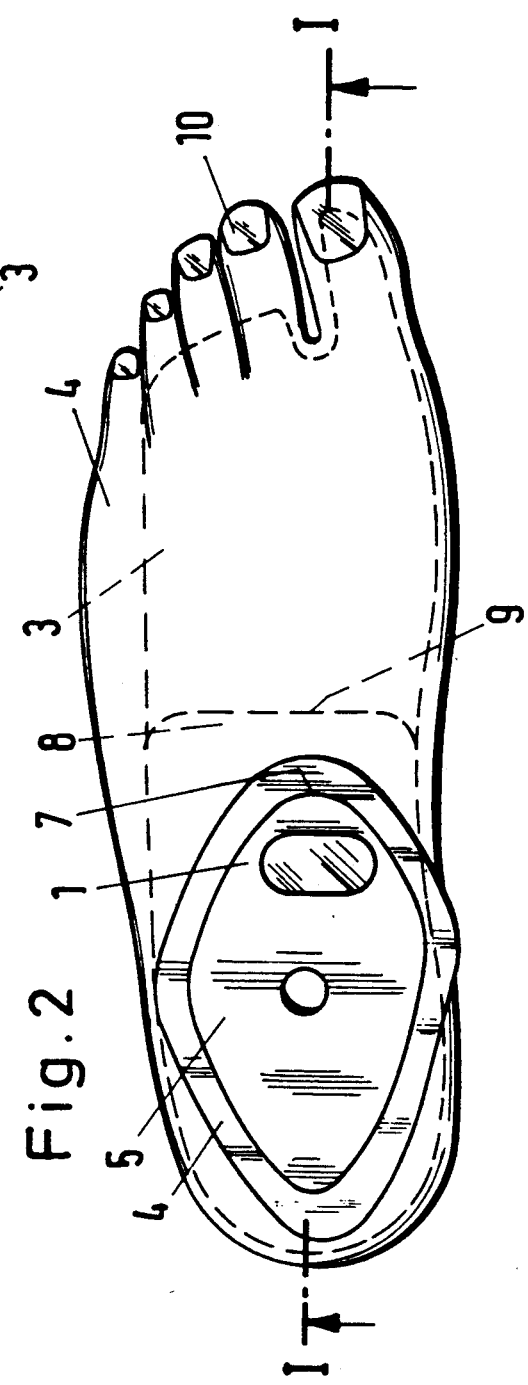
FIG. 2 shows a top plan view of the foot shown in FIG. 1.

The present invention is a foot comprising a core which starts from its front edge on the connecting surface, and extends into the instep region by an amount corresponding to less than half the length on the connecting surface. A flexible inner foot made of plastic foam, extending into the toe region and likewise enclosed by the skin-forming layer, adjoins the front surface of the core and the front side of the heel wedge. The skin-forming layer comprises a soft, easily deformable plastic foam layer, and thus the restoring forces of the skin-forming layer are less than the restoring forces of the inner foot.

The foot according to the present invention has a soft heel wedge. The skin-forming layer surrounding this heel part and the inner foot provided according to the invention is made very soft and does not substantially impair the elastic properties of the heel wedge or of the inner foot. Accordingly, the movement properties in the second phase of the rolling action when the heel is lifted are determined almost exclusively by the flexible properties of the inner foot. The skin-forming layer not only performs the function of protection against penetrating water and penetrating aggressive agents, it also enhances the cosmetic appearance of the foot surface. In contrast to the conventional skin-forming layer, the movement properties of the foot of the present invention are no longer substantially influenced by the skin-forming layer.

The inner foot of the artificial foot according to the present invention is shorter than the known inner foot disclosed in the Campbell Childs catalog. With the exception of the toe region, the inner foot of the present invention is surrounded by the skin-forming layer designed as a sheet-like enveloping layer, and therefore has no irregularities in its contour. The shape of the inner foot of the present invention corresponds essentially to the shape of the fore-foot in the instep and ankle regions.

An advantage of the foot according to the present invention is that the foot completely eliminates the need for additional stiffening means, such as elastic metal bands or the like. Consequently, the foot design is simple and inexpensive to produce. The foot has sufficient flexibility, even in the instep region, and can therefore fit into relatively narrow shoes and the like.

In an embodiment, the plastic foam of the skin-forming layer has a weight per unit volume of approximately 4 g/cm$^3$, the inner foot has a weight per unit volume of from about 6 to about 10 g/cm$^3$, and the heel wedge has a weight per unit volume of from about 2 to about 4 g/cm$^3$. At the same time, the core is preferably made very short, so that, starting from its front edge on the connecting surface, it extends into the instep region by an amount corresponding to less than one-third of its length on the connecting surface.

Preferably, in the foot design according to the present invention, the front tip of the heel wedge extends approximately up to the front edge of the core, and into the arch of the foot. This ensures resilience over a very wide range of the rolling action.

The artificial foot of the present invention as illustrated in the drawings, comprises a core 1 made of wood, a heel wedge 2, an inner foot 3 and a skin-forming layer 4 which surrounds the entire foot, with the exception of an upper connecting surface 5 of the core 1.

The core 1 is provided with an underside 6 which slopes upwards from the front to the rear and which provides room for the heel wedge 2 having an essentially triangular longitudinal section. The heel wedge 2 is composed of a soft plastic foam with a weight per unit volume of approximately 3 g/cm$^3$.

The core 1, beginning from a front edge 7 of the connecting surface 5, extends into the instep region of the foot with an extension 8 pointing obliquely downward and narrowing roundly. In an embodiment illustrated in the drawings, the distance between the front edge 9 of the extension 8 and the front edge 7 of the connecting surface 5 is approximately one-fifth of tee maximum length of the core 1 on the connecting surface 5. The inner foot 3 adjoining the contour of the extension 8 extends uniformly into the toe region of the foot. The shape of the inner foot corresponds approximately to the shape of the foot, since the skin-forming layer 4 surrounds the inner foot on all sides as a sheet-like enveloping layer, with the exception of variations in the wall thickness, such as can be seen, for example, in FIG. 3, occurring essentially for cosmetic reasons. The layer 4 surrounds the entire foot for practical purposes as a sheet-like enveloping layer, with the exception of the formation of the toes 10.

A bore 11 passes through the core 1 and heel wedge 2, widens in the manner of a step at the lower edge of the core 1 and serves for receiving a fastening screw having a screw head for attachment to an artificial leg. In the region of the larger diameter, the bore 11 is likewise provided with a thin wall of the skin-forming layer 4 so that no moisture or aggressive agents can penetrate into the inner structure of the foot, even from the bore 11. The wooden core 1 is sealed off by means of an insertable plastic sealing disk.

On the connecting surface 5, the core has a recess 12 which is filled with a cast resin 13 containing a filler. The recess 12 is disposed at the location which is regularly subject to stress by a connecting part during the rolling of the foot because increased wear of the core 1 occurs at this location. This wear is counteracted by introducing into the core the cast resin containing a filler.

What is claimed is:

1. An artificial foot comprising:
   a) a non-articulate incompressible core which comprises
      an underside which slopes upwards from front to rear of said foot,
      an upper connecting surface of a given length disposed in an ankle region of said foot for non-articulate ankle attachment of said foot to an artificial leg, and
      an extension forwardly extending into an instep region of said foot, said extension decreasing in height towards said front, wherein said core extends horizontally from a front edge on said upper connecting surface into said instep region only by an amount corresponding to less than about half of said length on said connecting surface;
   b) a heel wedge connected to said underside of said core;
   c) a non-articulate, unreinforced, flexible inner foot member adjoining both a front surface of said core within said instep region and a front side of said heel wedge, said inner foot member being flexible for substantial bending within said instep region and extending into a toe region of said foot, said core, said inner foot member and said heel wedge being interconnected without any articulate joints therebetween; and d) a soft, easily deformable skin-forming layer completely surrounding said core, said inner foot member and said heel wedge, with the exception of said upper connecting surface of said core, such that the restoring force of said skin-forming layer is less than the restoring force of said inner foot member;

wherein the elastic properties of said foot are determined solely by said inner foot member, said heel wedge and said skin-forming layer.

2. An artificial foot as claimed in claim 1, wherein said core comprises wood.

3. An artificial foot as claimed in claim 1, wherein said heel wedge comprises a soft plastic foam.

4. An artificial foot as claimed in claim 1, wherein said skin-forming layer comprises a plastic foam.

5. An artificial foot as claimed in claim 1, wherein said inner foot member comprises a plastic foam.

6. An artificial foot as claimed in claim 4, wherein said skin-forming layer comprises plastic foam having a weight per unit volume of approximately 4 g/cm$^3$.

7. An artificial foot as claimed in claim 1, wherein said inner foot member has a weight per unit volume of from about 6 to about 10 g/cm$^3$.

8. An artificial foot as claimed in claim 1, wherein said heel wedge has a weight per unit volume of from about 2 to about 4 g/cm$^3$.

9. An artificial foot as claimed in claim 1, wherein said core extends horizontally from said front edge on said upper connecting surface into said instep region by ones an amount corresponding to less than about one-third of the length on said connecting surface.

10. An artificial foot as claimed in claim 1, wherein a front tip of said heel wedge terminates approximately vertically flush with a front edge of said core.

11. An artificial foot as claimed in claim 1, wherein said skin-forming layer includes means for protecting penetration of water or an aggressive agent.

12. An artificial foot as claimed in claim 1, wherein said heel wedge has a weight per unit volume of approximately 3 g/cm$^3$.

13. An artificial non-articulate foot comprising:
a) a non-articulate incompressible core which comprises
   an underside which slopes upwards from front to rear of said foot,
   an upper connecting surface of a given length disposed in an ankle region of said foot for non-articulate ankle attachment of said foot to an artificial leg, and
   an extension forwardly extending into an instep region of said foot, said extension decreasing in height towards said front, wherein said core extends horizontally from a front edge on said upper connecting surface into said instep region only by an amount corresponding to less than about half of said length on said connecting surface;
b) a heel wedge connected to said underside of said core;
c) a non-articulate, unreinforced, flexible inner foot member adjoining both a front surface of said core within said instep region and a front side of said heel wedge, said inner foot member being flexible for substantial bending within said instep region and extending into a toe region of said foot, said core, said inner foot member and said heel wedge being interconnected without any articulate joints therebetween; and
d) a soft, easily deformable skin-forming layer completely surrounding said core, said inner foot member and said heel wedge, with the exception of said upper connecting surface of said core, such that the restoring force of said skin-forming layer is less than the restoring force of said inner foot member;

wherein said extension extends obliquely downward into said instep region and narrows roundly.

14. An artificial non-articulate foot comprising:
a) a non-articulate incompressible core which comprises
   an underside which slopes upwards from front to rear of said foot,
   an upper connecting surface of a given length disposed in an ankle region of said foot, and
   an extension forwardly extending into an instep region of said foot, said extension decreasing in height towards said front, wherein said core extends horizontally from a front edge on said upper connecting surface into said instep region only by an amount corresponding to less than about half of said length on said connecting surface;
b) a heel wedge connected to said underside of said core;
c) a non-articulate, unreinforced, flexible inner foot member adjoining both a front surface of said core within said instep region and a front side of said heel wedge, said inner foot member being flexible for substantial bending within said instep region and extending into a toe region of said foot, said core, said inner foot member and said heel wedge being interconnected without any articulate joints therebetween; and
d) a soft, easily deformable skin-forming layer completely surrounding said core, said inner foot member and said heel wedge, with the exception of said upper connecting surface of said core, such that the restoring force of said skin-forming layer is less than the restoring force of said inner foot member;

further comprising a bore vertically extending through said core and said heel wedge for non-articulate ankle attachment of said foot to an artificial leg at said upper connecting surface, wherein an interior surface of said bore is covered by a thin wall of said skin-forming layer.

15. An artificial foot comprising:
a) a non-articulate incompressible core which comprises
   an underside which slopes upwards from front to rear of said foot,
   an upper connecting surface of a given length disposed in an ankle region of said foot, for non-articulate ankle attachment of said foot to an artificial leg, and
   an extension forwardly extending into an instep region of said foot, said extension decreasing in height towards said front, wherein said core extends horizontally from a front edge on said upper connecting surface into said instep region only by an amount corresponding to less than about half of said length on said connecting surface;

b) a heel wedge connected to said underside of said core;

c) a non-articulate, unreinforced, flexible inner foot member adjoining both a front surface of said core within said instep region and a front side of said heel wedge, said inner foot member being flexible for substantial bending within said instep region and extending into a toe region of said foot, said core, said inner foot member and said heel wedge being interconnected without any articulate joints therebetween; and d) a soft, easily deformable skin-forming layer completely surrounding said core, said inner foot member and said heel wedge, with the exception of said upper connecting surface of said core, such that the restoring force of said skin-forming layer is less than the restoring force of said inner foot member;

wherein the forward portion of said foot consists essentially of said inner foot member and said skin-forming layer, whereby the movement properties of said foot producing rolling action when the heel is lifted are determined essentially exclusively by the flexible properties of said inner foot member.

16. An artificial foot as claimed in claim 15, wherein said skin-forming layer comprises plastic foam having a weight per unit volume of approximately 4 g/cm³.

17. An artificial foot as claimed in claim 15, wherein said inner foot member has a weight per unit volume of from about 6 to about 10 g/cm³.

18. An artificial foot as claimed in claim 15, wherein said heel wedge has a weight per unit volume of from about 2 to about 4 g/cm³.

19. An artificial foot comprising:

a) a non-articulate incompressible core which comprises
   an underside which slopes upwards from front to rear of said foot,
   an upper connecting surface disposed in an ankle region of said foot, for non-articulate ankle attachment of said foot to an artificial leg, and
   an extension forwardly extending into an instep region of said foot, said extension decreasing in height towards said front, wherein said core extends horizontally as measured from a rearmost portion of said foot into said instep region only by an amount corresponding to about half of the total horizontal length of said foot;

b) a heel wedge connected to said underside of said core;

c) a non-articulate, unreinforced, flexible inner foot member adjoining both a front surface of said core within said instep region and a front side of said heel wedge, said inner foot member being flexible for substantial bending within said instep region and extending into a toe region of said foot, said core, said inner foot member and said heel wedge being interconnected without any articulate joints therebetween; and d) a soft, easily deformable skin-forming layer completely surrounding said core, said inner foot member and said heel wedge, with the exception of said upper connecting surface of said core, such that the restoring force of said skin-forming layer is less than the restoring force of said inner foot member;

wherein the forward portion of said foot consists essentially of said inner foot member and said skin-forming layer, whereby the movement properties of said foot producing rolling action when the heel is lifted are determined essentially exclusively by the flexible properties of said inner foot member.

20. An artificial foot comprising:

a) a non-articulate incompressible core which comprises
   an underside which slopes upwards from front to rear of said foot,
   an upper connecting surface disposed in an ankle region of said foot, for non-articulate ankle attachment of said foot to an artificial leg, and
   an extension forwardly extending into an instep region of said foot and terminating rearward of a ball region of said foot;

b) a heel wedge connected to said underside of said core;

c) a non-articulate, unreinforced, flexible inner foot member adjoining both a front surface of said core within said instep region and a front side of said heel wedge, said inner foot member being flexible for substantial bending within said instep region and extending into a toe region of said foot, said core, said inner foot member and said heel wedge being interconnected without any articulate joints therebetween; and d) a soft, easily deformable skin-forming layer completely surrounding said core, said inner foot member and said heel wedge, with the exception of said upper connecting surface of said core, such that the restoring force of said skin-forming layer is less than the restoring force of said inner foot member;

wherein the forward portion of said foot consists essentially of said inner foot member and said skin-forming layer, whereby the movement properties of said foot producing rolling action when the heel is lifted are determined essentially exclusively by the flexible properties of said inner foot member.

* * * * *